US00PP29870P2

(12) United States Plant Patent
Garner

(10) Patent No.: US PP29,870 P2
(45) Date of Patent: Nov. 20, 2018

(54) ***ALOCASIA* PLANT NAMED 'DARK STAR'**

(50) Latin Name: ***Alocasia* hybrid**
Varietal Denomination: Dark Star

(71) Applicant: LariAnn Garner, Florida City, FL (US)

(72) Inventor: LariAnn Garner, Florida City, FL (US)

( * ) Notice: Subject to any disclaimer, the term of this patent is extended or adjusted under 35 U.S.C. 154(b) by 53 days.

(21) Appl. No.: 15/330,923

(22) Filed: Nov. 15, 2016

(51) Int. Cl.
*A01H 5/02* (2018.01)

(52) U.S. Cl.
USPC ..... Plt./373
CPC ..... *A01H 5/02* (2013.01)

(58) Field of Classification Search
USPC ..... Plt./373
See application file for complete search history.

*Primary Examiner* — Anne Marie Grunberg
(74) *Attorney, Agent, or Firm* — Penny J. Aguirre

(57) ABSTRACT

A new cultivar of *Alocasia* plant named 'Dark Star' that is characterized by its large plant size, its vigorous and robust growth habit, its large leaves that are green in color with dark grayish purple petioles and main leaf veins on the lower leaf surface, and its cold resistance to near freezing temperatures.

3 Drawing Sheets

Botanical classification: *Alocasia* hybrid.
Cultivar designation: 'Dark Star'.

BACKGROUND OF THE INVENTION

The present invention, *Alocasia* 'Dark Star', relates to a new and distinct interspecific hybrid of *Alocasia*, hereinafter referred to by its cultivar name, 'Dark Star'. 'Dark Star' is a new tropical plant used as a landscape and container plant.

The new cultivar was derived from a controlled breeding program conducted by the Inventor at a nursery in Florida City, Fla. The overall purpose of the breeding program is to make selections of *Alocasia* plants with dark colored petioles and leaf veins, cold tolerance combined with robust plants large in size. 'Dark Star' arose from a cross made in spring of 2012 between an unnamed and unpatented plant of *Alocasia odora* as the female parent and *Alocasia* 'Imperial Dark' (not patented) as the male parent. 'Dark Star' was selected as a single unique plant in spring of 2015 from amongst the seedlings derived from the above cross.

Asexual propagation of the new cultivar was first accomplished in Eustis, Fla. in 2015 using In vito propagation initiated using meristematic cell tissue culture under the direction of the Inventor. Asexual propagation by in vitro propagation has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Dark Star' as a new and unique cultivar of *Alocasia*.

1. 'Dark Star' exhibits a large plant size.
2. 'Dark Star' exhibits a vigorous and robust growth habit.
3. 'Dark Star' exhibits large leaves that are green in color with dark grayish purple petioles and main leaf veins on the lower leaf surface.

4. 'Dark Star' exhibits cold resistance to near-freezing temperatures.

The female parent of 'Dark Star' differs from 'Dark Star' in having petioles and main leaf veins that are green in color and in having a smaller plant size. The male parent of 'Dark Star', 'Imperial Dark', is similar to 'Dark Star' in having petioles that are dark in color. 'Imperial Dark' differs from 'Dark Star' in being cold susceptible and sustaining damage following exposure to near-freezing temperatures. 'Dark Star' can be most closely compared to the *Alocasia macrorrhizos* cultivars 'Black Petioled' (not patented) and 'Borneo Giant' (not patented). 'Black Petioled' is similar to 'Dark Star' in having petioles and main leaf veins that are dark in color. 'Black Petioled' differs from 'Dark Star' in having leaves that are smaller in size, in having a smaller overall plant size, and in being susceptible to near-freezing temperatures. 'Borneo Giant' is similar to 'Dark Star' in having a large overall plant size and robust growth habit. 'Borneo Giant' differs from 'Dark Star' in having petioles and main leaf veins that are green in color and in being susceptible to near freezing temperatures.

BRIEF DESCRIPTION OF THE DRAWINGS

The accompanying colored photographs illustrate the overall appearance and distinct characteristics of the new *Alocasia*, 'Dark Star'. The photographs were taken of an 8-month-old plant of 'Dark Star' as grown in a greenhouse under 2-mm poly and then planted outdoors in the ground in Apopka, Fla.

Figure 1:
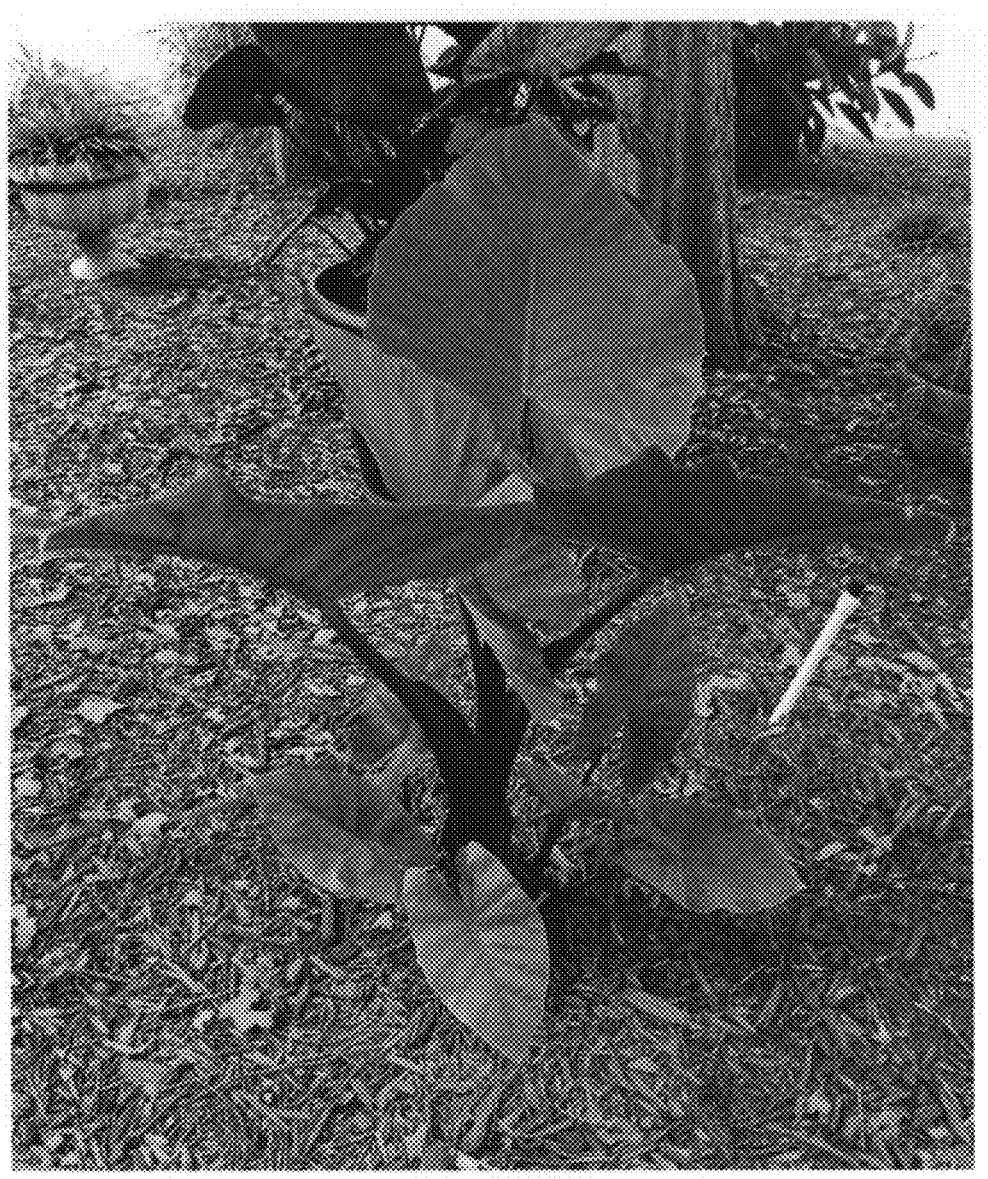
FIG. 1 provides a view of the plant habit and dark petioles of 'Dark Star'.
Figure 2:
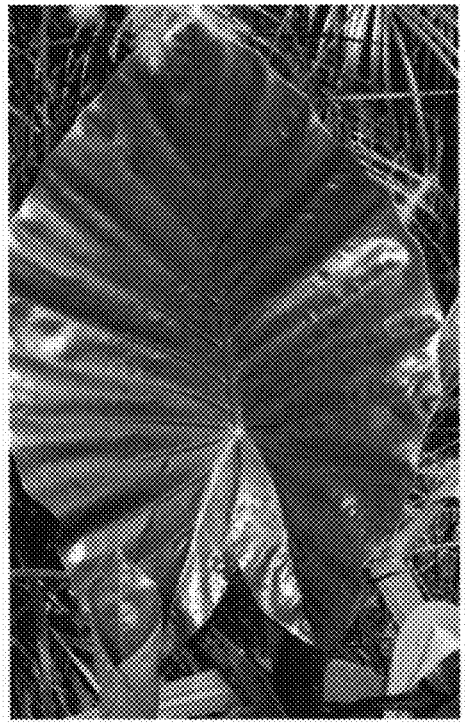

The photograph in FIG. 2 provides a close-up view of the upper surface of a leaf of 'Dark Star'.

Figure 3:
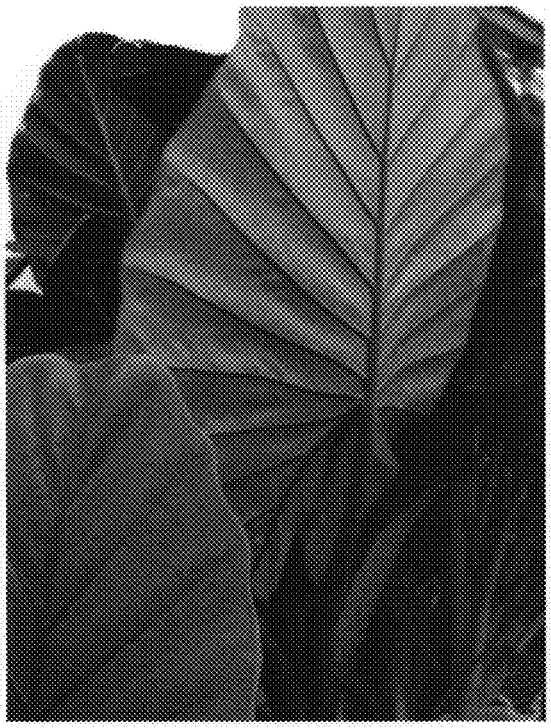

The photograph in FIG. 3 provides a close-up view of the lower surface of a mature leaf of 'Dark Star'.

Figure 4:
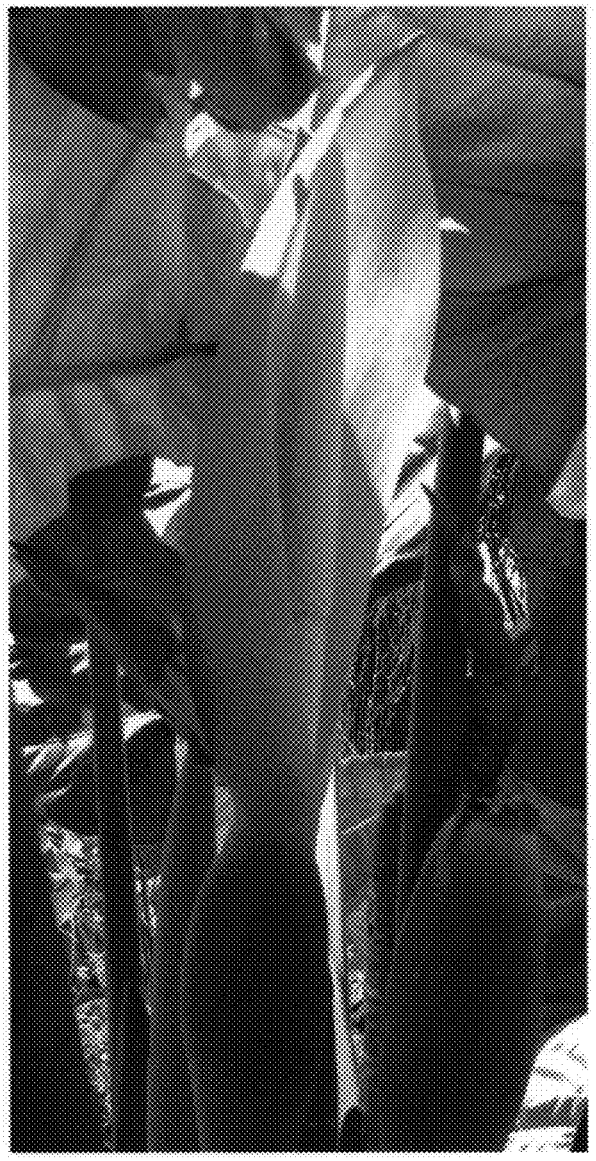

The photograph in FIG. 4 provides a close-up view of the inflorescence of 'Dark Star'.

The colors in the photographs are as close as possible with the photographic and printing technology utilized and the color values cited in the Detailed Botanical Description accurately describe the colors of the new *Alocasia*.

DETAILED BOTANICAL DESCRIPTION OF THE PLANT

The following is a detailed description of 8-month-old plants of the new cultivar as grown in a greenhouse under 2-mm poly and then planted outdoors in the ground in Apopka, Fla. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Approximately 6 weeks in the fall in south Florida.

*Plant type.*—Tropical perennial herb.

*Plant habit.*—Upright, stemless.

*Height and spread.*—Up to an average 1.8 m in height and 2.1 m in width at maturity.

*Cold hardiness.*—At least to U.S.D.A. Zone 9 and resistance to near freezing temperatures.

*Diseases and pests.*—Resistance to root rot (*Pythium* spp.) has been observed.

*Roots.*—Fibrous and fine, 155A in color.

*Propagation type.*—Tissue culture.

*Growth rate.*—Vigorous.

*Time required for root development.*—An average of 14 days for root initiation with a rooted cutting produced after an average of four weeks.

*Stem description.*—Rhizome-like trunk formed at the base of the petioles with age (see petiole description).

Foliage description:

*Leaf shape.*—Cordate-sagittate.

*Leaf division.*—Single.

*Leaf base.*—Sagittate, deeply cut; lobes about 15 cm in length and width.

*Leaf apex.*—Cuspidate.

*Leaf venation.*—Pinnate, color; young leaves upper and lower surfaces 144C, mature leaves upper surface 143A to 143B and lower surface N186A to N186B, conspicuous on both surfaces, particularly on lower surface.

*Leaf margins.*—Undulate.

*Leaf attachment.*—Petiolate.

*Leaf arrangement.*—Emerge basally with petioles conduplicate.

*Leaf surface.*—Upper surface; coriaceous, glabrous, and glossy, lower surface; coriaceous, glabrous, and dull.

*Leaf orientation.*—Held vertical to horizontal to the petiole.

*Leaf color.*—Young leaves; upper and lower surfaces 144C to 144D, mature leaves; upper surface 143A to 143B and lower surface 138A to 138B.

*Leaf size.*—An average of 45 cm in length and 32 cm in width.

*Leaf sinus.*—An average of 15 cm in depth and 2 cm in width.

*Petioles.*—Held erect to semi-erect, an average of 47 cm in length, 1.3 cm in distal diameter and 3.5 cm in basal diameter, glabrous, coriaceous surface, color; 138B heavily suffused with N186A to N186B, rhizome-like base; about 5 cm in length and 2.7 cm in width, comprised of petiole scales, surface is rough and paper-like, color is a blend of N167B and 163A to 163C, trunk with petiole scales removed N170D and with scars 198D.

Inflorescence description:

*Inflorescence type.*—Spadix surrounded by a spathe, male portion held above female portion, only female flowers are developed.

*Inflorescence size.*—An average of 17 cm in length and 1.9 cm in width.

*Inflorescence bud.*—Linear to slightly narrow lanceolate in shape, an average of 14 cm in length and 1.2 cm in width, color; 144A to 144D.

*Flower fragrance.*—Slight sweet fragrance.

*Lastingness of inflorescence.*—Inflorescence blooms intermittently during the bloom period, individual flowers last about 2 to 3 weeks.

*Inflorescence/flower quantity.*—An average of 120 female flowers sessile to spadix, sessile male flowers are undeveloped.

*Spathe.*—Hooded, bract, subtending spadix, an average of 15.4 cm in length and 5.5 cm in width, entire margin, bottom portion; elliptic in shape, an average of 2.9 cm in length and 2.2 cm in width, apex fused to upper portion, truncate base, upper portion (hood); rotund to oval in shape, an average of 12.5 cm in length and 5.5 cm in width, cuspidate apex, all surfaces coriaceous, glabrous, and smooth, upper and lower portion outer surface glaucescent, lower portion inner surface; glossy, color; upper portion outer surface 150C to 150D and inner surface 150D, lower portion outer surface 137A to 137B and inner surface 144C to 144D.

*Spadix.*—Male portion above female zone; upright linear in shape (phallus like), apex narrowly pointed, an average of 13.1 cm in length and 1.3 mm in width, 159B towards the top and 158A towards the base, female portion; ovate in shape, an average of 2 cm in length and 1.2 cm in width, a mix of 144A and 158B in color.

*Peduncle.*—Grows from base of plant, oval in shape, an average of 14 cm in length and 9 mm in diameter, durable and strong, 143A in color, coriaceous, glabrous and smooth surface.

Reproductive organs:

*Gynoecium.*—1 pistil with sessile, discoid stigmas 158B in color, monocarpous ovary is round in shape and full of many minute ovules; oval in shape and translucent NN155D in color.

*Androecium.*—Undeveloped on plants observed, pollen was not observed but a low quantity of pollen has been observed on mature plants not available for data collection.

*Fruit and seed.*—None observed.

It is claimed:

1. A new and distinct cultivar of *Alocasia* plant named 'Dark Star' as herein illustrated and described.

* * * * *